(12) United States Patent
Tröndle

(10) Patent No.: US 10,327,795 B2
(45) Date of Patent: Jun. 25, 2019

(54) CONNECTION FOR A MORCELLATOR

(71) Applicant: TROKAMED GMBH, Geisingen (DE)

(72) Inventor: Karlheinz Tröndle, Geisingen (DE)

(73) Assignee: TROKAMED GMBH, Geisingen (DE)

( * ) Notice: Subject to any disclaimer, the term of this patent is extended or adjusted under 35 U.S.C. 154(b) by 422 days.

(21) Appl. No.: 14/891,455

(22) PCT Filed: May 14, 2014

(86) PCT No.: PCT/EP2014/059863
§ 371 (c)(1),
(2) Date: Nov. 16, 2015

(87) PCT Pub. No.: WO2014/184251
PCT Pub. Date: Nov. 20, 2014

(65) Prior Publication Data
US 2016/0095613 A1 Apr. 7, 2016

(30) Foreign Application Priority Data

May 17, 2013 (DE) .................... 20 2013 102 186 U
Aug. 16, 2013 (DE) .................... 20 2013 007 298 U

(51) Int. Cl.
| | | |
|---|---|---|
| A61B 17/32 | (2006.01) | |
| A61B 17/34 | (2006.01) | |
| A61B 17/00 | (2006.01) | |
| A61B 19/00 | (2006.01) | |

(52) U.S. Cl.
CPC .... *A61B 17/32002* (2013.01); *A61B 17/3496* (2013.01); *A61B 2017/0046* (2013.01); *A61B 2017/00455* (2013.01); *A61B 2017/00477* (2013.01); *A61B 2017/320024* (2013.01); *A61B 2019/481* (2013.01)

(58) Field of Classification Search
CPC ...... A61B 17/32002; A61B 17/320024; A61B 2017/0046; A61B 2017/00477
USPC ........................................... 606/171
See application file for complete search history.

(56) References Cited

U.S. PATENT DOCUMENTS

| | | | |
|---|---|---|---|
| 4,461,305 A | 7/1984 | Cibley | |
| 2005/0010238 A1 | 1/2005 | Potter et al. | |
| 2008/0039884 A1 | 2/2008 | Nohilly et al. | |
| 2010/0160823 A1* | 6/2010 | Parihar | A61B 10/0275 600/567 |
| 2011/0251597 A1 | 10/2011 | Bharadwaj et al. | |

FOREIGN PATENT DOCUMENTS

| | | |
|---|---|---|
| DE | 102008036420 A1 | 2/2010 |
| DE | 102010037974 A1 | 4/2012 |
| DE | 202013102186 U1 | 6/2013 |

OTHER PUBLICATIONS

International Search Report for PCT/EP2014/059863 dated Jul. 22, 2014.

* cited by examiner

*Primary Examiner* — Melanie R Tyson
(74) *Attorney, Agent, or Firm* — Bachman & LaPointe, PC

(57) ABSTRACT

A connecting element for a morcellator (M). The morcellator (M) has a hand module (1), a cutting tube (5) and a sleeve (8), the hand module (1) has a connecting piece (10) and the sleeve (8) has a connecting ring (9). The connecting ring (9) can be clipped onto the connecting piece (10).

10 Claims, 15 Drawing Sheets

CONNECTION FOR A MORCELLATOR

BACKGROUND OF THE INVENTION

The invention relates to a connection for a morcellator and to a protective sleeve for a medical instrument.

Various connections for morcellators are known and customary in the prior art. The invention can be used wherever a rotating cutting tube, which is configured in particular as a cutting tube, is used to carry out an activity in the body of a living being. Medical instruments of this type are currently used especially in endoscopic interventions. They are used to remove relatively large portions of tissue.

The morcellator especially has, as cutting tube, a cutting tube which has a cutting edge at the distal end. Said cutting tube is introduced into the body, for example, through an endoscope and is then rotated. By this means, the cutting edge removes portions of tissue which are then removed from the body through the cutting tube itself. For this purpose, the tissue part can be sucked off or else also removed by a further medical instrument which is then guided, for example, through a valve module into the cutting tube and through the latter.

A morcellator according to the prior art is described in particular in DE 10 2010 037 974 A1. The intention is that the present invention is a development of the morcellator shown there.

Protective sleeves known according to the prior art have two substantial disadvantages. Firstly, they cannot be connected to the handpiece in a simple manner. Secondly, known protective sleeves are not suitable for preventing gas from passing therethrough if the medical appliance is not mounted in the protective sleeve and therefore seals off the latter. Furthermore, known protective sleeves are inflexible in that they are not suitable for use with medical appliances having diameters which greatly differ from one another. It is also frequently not possible to ensure a sealing function for medical appliances having diameters which greatly differ from one another.

In order to be able to work within the scope of minimally invasive surgery in the body interior, a surgeon requires an access route into the body interior, for example to the abdominal cavity. In order to be able to work with sufficient space and at the same time as little injury as possible to a patient's tissue, in the case of minimally invasive operations gas is generally insufflated, the gas raising the skin, for example the abdominal wall in the case of operations in the region of the abdominal cavity, as a result of which the surgeon has sufficient space for carrying out the operation. Medical and in particular surgical instruments are generally used together with a protective sleeve which surrounds said instruments and prevents undesirable damage to intact tissue. In the simplest case, such a protective sleeve is a hollow tube. In order to mount the protective sleeve securely during an operation, the protective sleeve generally has a connecting device by means of which said protective sleeve can be connected to a handpiece of a medical and in particular surgical instrument.

A protective sleeve according to the prior art is disclosed, for example, in DE 20 2013 102 186 for use with a morcellator.

It is the object of the invention to provide a connection for a morcellator according to DE 10 2010 037 974 A1, which further simplifies the handling by the user, and therefore to contribute to increasing the safety during use.

It is furthermore the object of the present invention to overcome the disadvantages of the prior art. In particular, the intention is to provide a protective sleeve for a medical instrument, which protective sleeve prevents gas from passing through the medical instrument and also assists the guiding of the medical instrument in the protective sleeve.

SUMMARY OF THE INVENTION

The foregoing objects are achieved by the present invention.

First of all, reference is made with respect to the details to the disclosure of DE 10 2010 037 974 A1. A morcellator according to the invention is described there. The disclosure of DE 10 2010 037 974 A1 is intended to be considered in particular as being integrated as part of this document.

A connecting element according to the invention serves for connecting to a morcellator. The morcellator here has a hand module, a cutting tube and a sleeve. The hand module in turn has a connecting piece. The sleeve has a connecting ring. The connecting ring can be clipped onto the connecting piece. This means in particular that the sleeve can be connected to the hand module by clipping thereon. This preferably takes place by means of a rocker latch which can be actuated manually. The internal circumference of the connecting ring is enlarged by means of the rocker latch. After the connecting ring has been placed onto the connecting piece, the rocker latch is released and engages in a groove of the connecting piece. The connecting ring is thereby connected to the connecting piece.

In addition, the connecting piece comprises a flange-mounted ring with a recess. The flange-mounted ring can preferably have a plurality of recesses. The latter are either distributed over part of the circumference of the flange-mounted ring or are distributed over the entire circumference of the flange-mounted ring. The number of recesses on the flange-mounted ring is as desired. A flange cam can be brought into engagement with the recesses of the connecting piece.

This leads to the connecting ring being fixed at a certain point of the circumference of the connecting piece by selecting a certain recess and introducing the flange cam into the recess. The flange cam furthermore substantially forms a line with a covering of the sleeve. The covering constitutes an extension of the circumference of the sleeve on a portion thereof. The covering is required in order, in the case of a rotating cutting tube, not to transmit any rotational movements to the treated tissue. By this means, the treated tissue cannot be secured to a cutting edge and rotate therewith since the covering engages over a certain region of a cutting edge.

A connecting element according to the invention furthermore has a position indicator in the form of a bead. The bead here indicates the position of the flange cam and therefore of the covering. If, for example, a recess at 12 o'clock is selected on the flange ring, the user even during use, i.e. when the covering is in the interior of the human body, knows where the covering is located. If the connecting ring and the connecting piece should then be uncoupled in order to transfer the flange cam into another recess of the flange ring, the user would have more comfortable manual control under some circumstances. This, in turn, would make his work easier. The user has a precise positional indication of the covering by means of the bead. Furthermore, the cutting tube can be clipped to the hand module via a latching cam. The latching cam engages here in a corresponding recess within the hand module.

In addition, an actuating button is present on the hand module. The actuating button brings about a screwing movement of the connecting piece on the hand module. In the state when the connecting ring is clipped onto the connecting piece, not only the connecting piece, but also the connecting ring with the associated sleeve is moved away from the hand module or toward the hand module. This depends on the position desired in each case by the actuating button. The effect also achieved by spacing the connecting piece and the connecting ring connected thereto from the hand module is that the sleeve is pushed over the cutting edge. During a reversible actuation, the sleeve in turn is pulled toward the hand module and releases part of the cutting edge again.

This means that, for example, the hand module can always remain the same while the cutting tube is exchanged. The cutting tube can be exchanged for an identical cutting tube in the event of wear or soiling, but the use of differently configured cutting tubes for different medical activities is also conceivable.

In a preferred exemplary embodiment of the invention, the cutting tube is designed to be hollow and is connected rotatably about the axis thereof to the hand module.

The releasable connection between cutting tube and hand module is preferably intended to be configured as a latching connection. This means that the cutting tube is simply inserted into the hand module and undergoes a latching or click closure. Similarly, the cutting tube can be removed from the hand module by either pulling on the cutting tube and/or on the hand module.

A latching connection is brought about by a latch which is preferably designed as a latching spring being arranged on an element, the latch interacting with a corresponding latching cam in the hand module. The latch or latching spring here can even be formed from the cutting tube and is preferably of self-springing design such that it yields inward when the cutting tube is inserted into the hand module and then snaps behind the latching cam. Similarly, said latch or latching spring yields inward when the cutting tube is pulled out of the hand module and passes over the latching cam. The latching cam here can be provided in annular form as an inner ring in a receiving element in the hand module, but other possibilities are also conceivable.

Furthermore, an external toothed ring which interacts with an internal toothed ring in the hand module is intended to be assigned to the cutting tube. Said internal toothed ring is connected via a ring bevel gear to a bevel driving gear which, in turn, preferably sits on an axis of rotation of a rotor. By this means, the rotational movement of the axis of rotation is transmitted to the cutting tube.

For support during rotation, two spaced-apart sliding bearing rings which rotate in corresponding plain bearings in the receiving element in the hand module are preferably placed on the cutting tube.

Protection is also sought independently for the arrangement described last since it is envisaged that the cutting tube is mounted with the sliding rings in the plain bearings with at least 0.2 Nm, but with at maximum 5 Nm. The sliding rings are pressed non-positively onto the cutting tube, and it is furthermore conceivable for the cutting tube to be of multi-part design, in particular in the proximal region which is inserted into the hand module.

A further concept of the present invention relates to the configuration of the distal end of the cutting tube. A portion of hardened flat steel which also forms the cutting edge is intended to be provided here. There is the possibility here for said cutting element formed from flat steel to radially encompass the cutting tube or to be inserted into the cutting tube. Furthermore, said cutting element can also be directly butt-joined onto the cutting tube.

A valve unit is preferably inserted on that side of the hand module which is opposite the cutting tube. Said valve unit can enter into a bayonet-like connection with the hand module. The valve unit contains a valve which permits a further medical instrument to be inserted, but surrounds said instrument as air-tightly as possible.

A medical instrument within the context of this invention is preferably a surgical instrument, in particular an instrument used within the scope of minimally invasive surgery. By way of example, but not exclusively, a morcellator may be mentioned here.

All protective sleeves which are customary in minimally invasive surgery and have a connecting device can be configured in accordance with the present invention, and therefore the invention is not restricted to special protective sleeves for individual applications.

In the simplest exemplary embodiment, a protective sleeve is a hollow tube.

However, according to a preferred exemplary embodiment, the protective sleeve is configured to be matched to the function thereof during an operation. It is possible here to conceive of a covering at the distal end of the protective sleeve, i.e. the end which is oriented toward the patient in the use position. This covering is a partial extension of the sleeve. If a medical instrument emerges only by a short piece out of the protective sleeve at the distal end, the covering permits certain tissue regions to be shielded from the medical instrument since, as viewed in cross section, part of the medical instrument is covered by the protective sleeve or by the covering and cannot act on the tissue.

The protective sleeve preferably has a connecting device at the proximal end thereof, i.e. the end which, in the use position, for example during an operation, faces away from the patient. Devices which can be connected simply and securely to a corresponding device on the handpiece and can be released from said device again are preferably suitable here.

Simple production and release of the connection between handpiece and protective sleeve is highly desirable within the scope of modern minimally invasive operation methods since, for example, simple and rapid cleaning of medical instruments during the operation is therefore made possible. Furthermore, the same protective sleeve can therefore be used for a plurality of medical instruments during just one operation, as a result of which the risk of the operation can be reduced and time can be saved.

It should be mentioned here that the present invention is also intended to cover embodiments in which the medical instrument and the handpiece are formed integrally.

According to an exemplary embodiment, the connecting device assigned to the protective sleeve is a connecting ring, and the corresponding device assigned to the handpiece is a connecting piece. Connecting ring and connecting piece together form a connecting element.

The connecting ring can preferably be clipped here onto the connecting piece. This means in particular that the protective sleeve can be connected to the handpiece by being clipped thereon. This takes place, for example, by means of a rocker latch which can be actuated manually. The internal circumference of the connecting ring is increased by the rocker latch. After the connecting ring has been placed onto the connecting piece, the rocker latch is released and engages in a groove of the connecting piece. The connecting ring is thereby connected to the connecting piece.

However, it is also possible to conceive of different ways of providing a connection.

According to the invention, an above-described protective sleeve with a connecting device is assigned a lock unit. In a simple exemplary embodiment, the lock unit is a valve or a sealing element.

In general, it is possible to conceive both of a lock unit for disposable use and a reuseable lock unit.

However, the lock unit is preferably designed as a lock system which consists of at least one valve and at least one sealing element. Valve and sealing element here are preferably assigned to each other. The lock unit or the lock system is assigned here to the proximal end of the protective sleeve or to the connecting device. The lock unit or the lock system is furthermore assigned preferably reversibly, that is to say removably and re-connectably, to the connecting device. This assignment preferably takes place by means of a rapid-action closure. Respectively corresponding elements of a rapid-action closure are integrally formed here on the proximal end of the protective sleeve and of the lock unit or the lock system. Furthermore, however, it is also possible to conceive of other types of connection, for example all types of plugging on or clipping on. Furthermore, it is also possible to conceive of screwing on, with lock unit and connecting element having corresponding threads. Furthermore, other non-positive or positive types of connection are also suitable.

Furthermore, the assignment of the lock unit or of the lock system to the protective sleeve preferably takes place via the valve, with the above-listed types of connection being used. The sealing element is assigned in turn to the valve. The sealing element is also assigned to the valve preferably in a releasable and re-connectable manner.

The sealing element is preferably composed of a reversibly deformable material, for example of a deformable or flexible plastic. For example, elastomers or materials which behave in a similar manner are suitable in this case.

The sealing element has, at a distal end, a bead which can enter into a positive connection with a proximal-end groove of the valve. At least one tab is furthermore preferably integrally formed on the sealing element, but two tabs are particularly preferably integrally formed thereon. These tabs are protrusions which are formed integrally with the sealing element and preferably have elevations for better handling. While the sealing element can be brought into positive connection with the valve by means of pressure, said connection is released again by pulling on the tab or on the tabs.

The sealing element furthermore has, substantially centrally, a recess through which a medical instrument, but also, for example, an optical instrument, can pass. Said instrument is then furthermore introduced into the protective sleeve in the distal direction, wherein said instrument passes the valve and emerges from the protective sleeve at the distal end thereof. The sealing element can fulfill two functions here. Firstly, it can serve for sealing, by the instrument passing through the recess in such a manner that said instrument lies or is guided flush and therefore in a substantially air or gas-tight manner in the recess. The sealing function is preferably assisted or simplified here by the use of a flexible or deformable material. Secondly, the sealing element can serve for guiding a medical instrument. This is suitable in particular in the case of instruments, the diameter or shaft diameter of which is significantly smaller than the diameter of an internal cavity of the protective sleeve or of the tube. Instruments of this type can be guided centrally and securely in the tube or used together therewith by the use of the sealing element.

In a simple exemplary embodiment, the valve is formed in one piece. Preferably, however, the valve is formed in a number of pieces, wherein at least one receptacle and a sealing unit are included. The sealing unit here is mounted in the receptacle in the use position. The receptacle is furthermore preferably configured in two pieces and consists of upper part and lower part which interact as a valve housing. Upper and lower part are preferably provided with corresponding threads. Upper and lower part can therefore be unscrewed, the sealing unit inserted, and upper and lower part screwed together again in order to obtain a valve which is ready for use. This also permits exchange of the sealing unit without having to exchange the entire valve. Of course, it is also possible to conceive of connecting upper and lower part of the valve in a different manner than by screwing; for example, all types of known rapid-action closures are suitable here.

The sealing unit preferably comprises at least two sealing lips. In the use position, i.e., for example, during an operation, the sealing lips here fulfill a sealing function by preventing the passage of gas through the protective sleeve in the direction of the proximal end. For example, the abdominal cavity can therefore be kept in the insufflated state, i.e. in the state partially filled with gas and therefore ready for the operation. A configuration of four sealing lips is particularly preferred here.

The lock system or valve and sealing element preferably fulfill a plurality of functions.

Firstly, the valve permits the above-described sealing function of the location, at which the minimally invasive operation takes place, in relation to the surroundings, for example an operating theater. The sealing element furthermore contributes to an additional sealing function. The sealing element can be connected to the valve in a substantially air- or gas-tight manner by the bead of the sealing element interacting with the corresponding groove of the valve in such a manner that air cannot pass between those regions of bead and groove which come to lie on each other.

Secondly, the sealing element first of all permits additional sealing between distal and proximal end of the protective sleeve. Furthermore, the sealing element also permits the guidance of an instrument passing through the recess.

Finally, it should be emphasized that a particular advantage of a protective sleeve according to the invention can be seen in the fact that said protective sleeve can be designed to be lightweight and short, but at the same time, with the lock unit, has a device by means of which a gas-tight separation is provided, for example between body cavity and operating theater. In a starting position in which the protective sleeve, although assembled and preferably connected to the lock unit, has not yet received a medical instrument, said protective sleeve is therefore suitable for closing an insufflated body cavity.

By means of the use of a rapid-action closure for connecting lock unit and protective sleeve or connecting device, the present protective sleeve can be adapted rapidly to various situations and requirements of modern minimally invasive surgical practice.

BRIEF DESCRIPTION OF THE DRAWINGS

Further advantages, features and details emerge from the description below of an exemplary embodiment according to the invention. In the figures, in particular.

DETAILED DESCRIPTION

Figure 1:
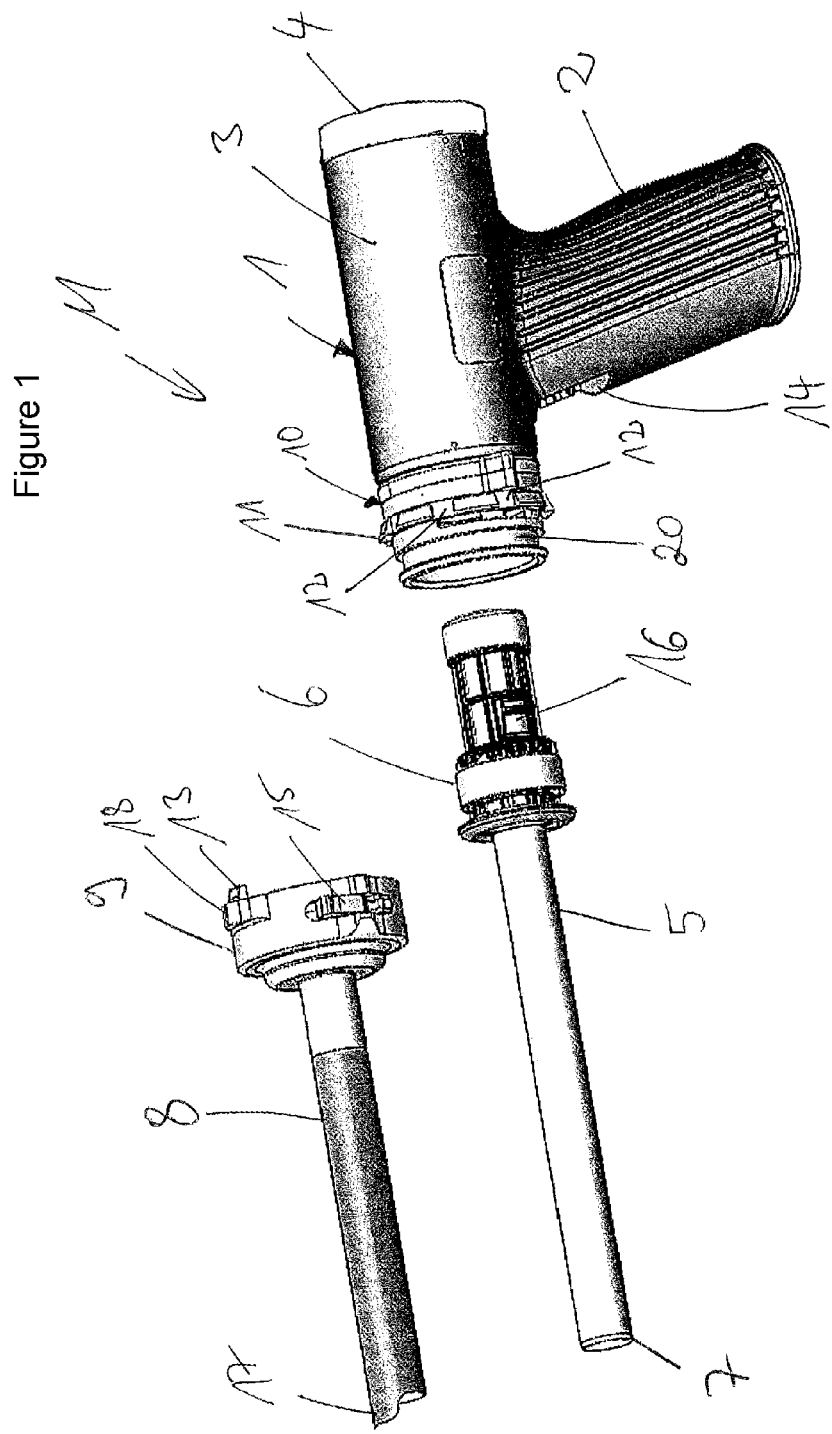
FIG. 1: shows a dismantled morcellator.

FIG. 1 shows a connecting element according to the invention for a morcellator M. The connecting element consists of a connecting ring 9 and a connecting piece 10. In this exemplary embodiment, the connecting ring 9 is part of a sleeve 8 whereas the connecting piece is part of a hand module 1. The morcellator M consists here of the hand module 1, a cutting tube 5 and the sleeve 8. The connecting ring 9 can be clipped onto the connecting piece. This means that, as a rule, the internal circumference of the connecting ring is larger than the external circumference of the connecting piece 10.

In addition, a flange-mounted ring 11 which is formed as part of the connecting piece 9 can be seen. The flange-mounted ring 11 has various recesses 12. Said various recesses 12 are distributed here over the entire circumference of the flange-mounted ring 11. Furthermore, a flange cam 13 which is formed as part of the connecting ring 9 can be seen. FIG. 1 furthermore shows that the cutting tube 5 does not have a cutting edge 7 at the distal end. Also shown is a driving connection 6 which can be connected to the hand module 1 via a latching cam 16. In the region of the guiding part 3, the hand module 1 has a drive and a gearing which leads to the cutting edge 7 being able to be set into rotation. Furthermore, a valve module 4 can be seen. The valve module 4 is attached here to the connecting piece 10 at the other end of the guiding part 3. In addition to the guiding part 3, the hand module 1 also has a handle part 2. The handle part 2 in turn comprises an actuating button 14. Furthermore, FIG. 1 shows a rocker latch 15 which, by manual actuation, increases the internal circumference of the connecting ring 9 and therefore permits the connecting ring 9 to be placed onto the connecting piece 10. After the connecting ring 9 is placed onto the connecting piece 10, the rocker latch 15 can be released again manually. Said rocker latch is then pressed via a spring mechanism into a groove 20 of the connecting piece 10 and therefore secures the connecting ring 9 on the connecting piece 10.

Figure 2:
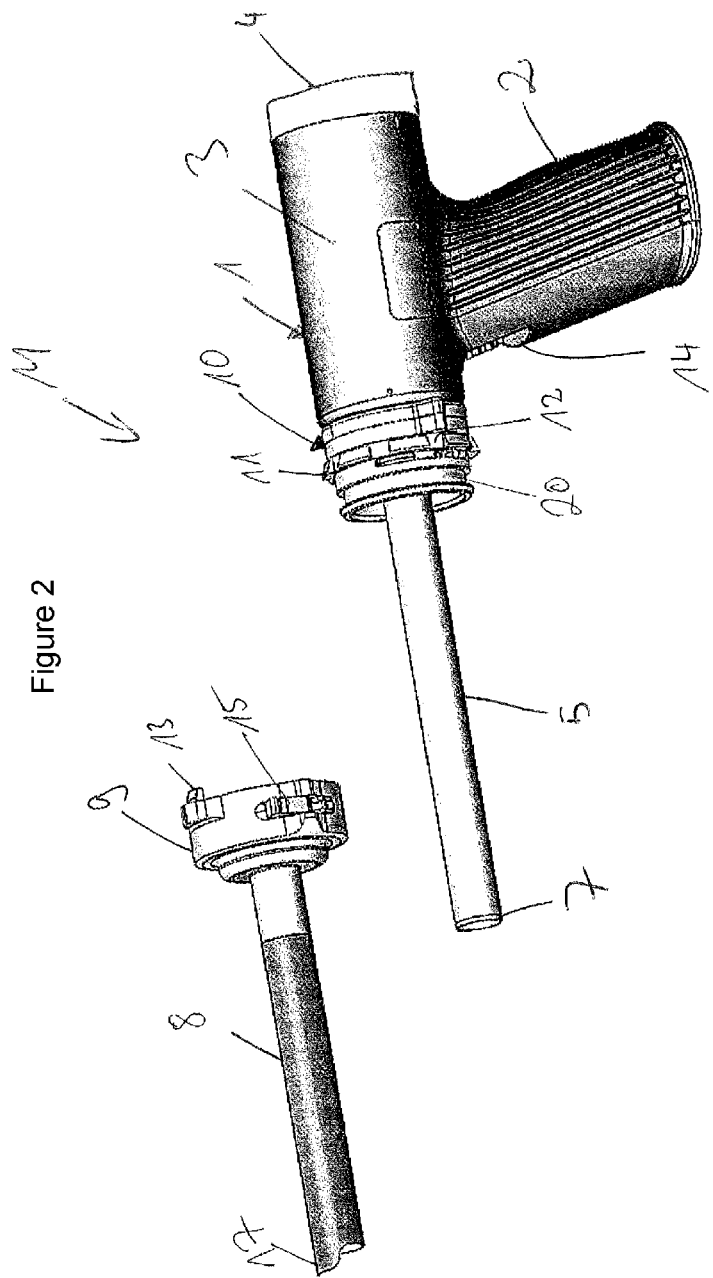
FIG. 2: shows a partially dismantled morcellator according to FIG. 1.

FIG. 2 shows how the cutting tube 5 with the associated features is clipped into the guiding part 3. Furthermore, it can be seen how the sleeve 8 has a covering 17 at the other end of the connecting ring 9. The covering 17 here substantially forms a line with the flange cam 13. The covering 17 is a partial extension of the circumference of the sleeve 8 at the distal end.

Figure 3:
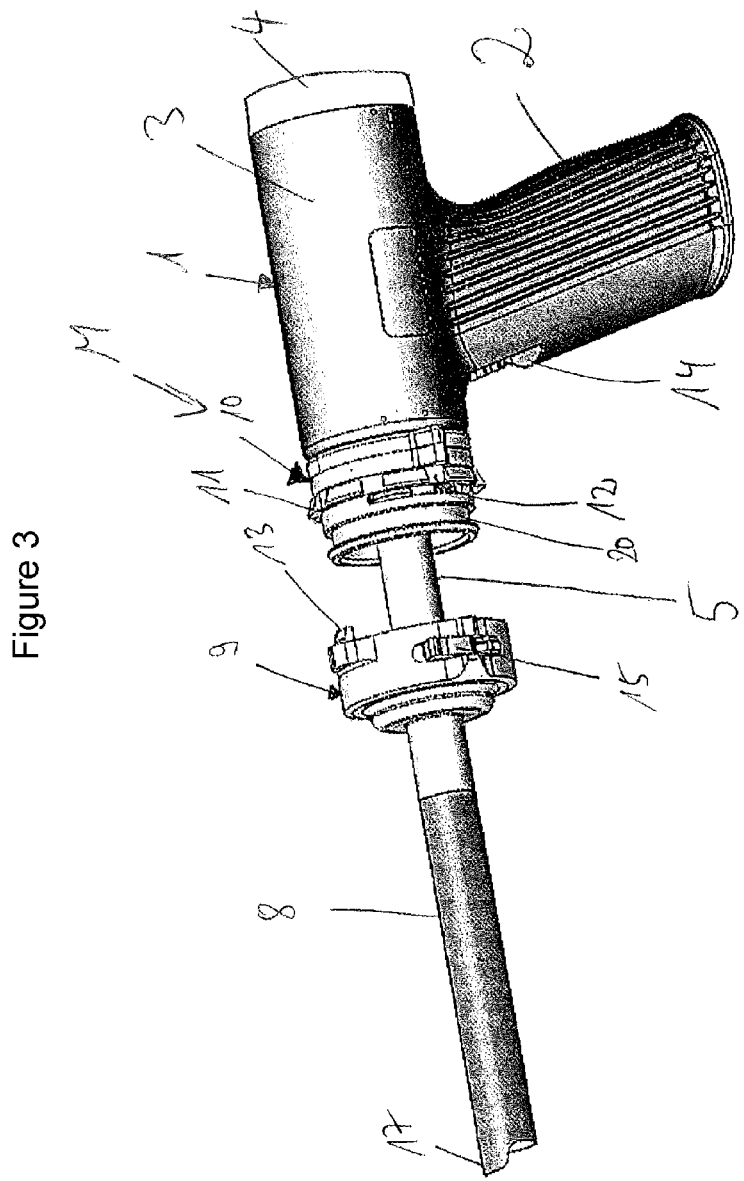
FIG. 3: shows a partially dismantled morcellator.

It is now shown in FIG. 3 how the sleeve 8 has been partially pulled onto the cutting tube 5.

Figure 4:
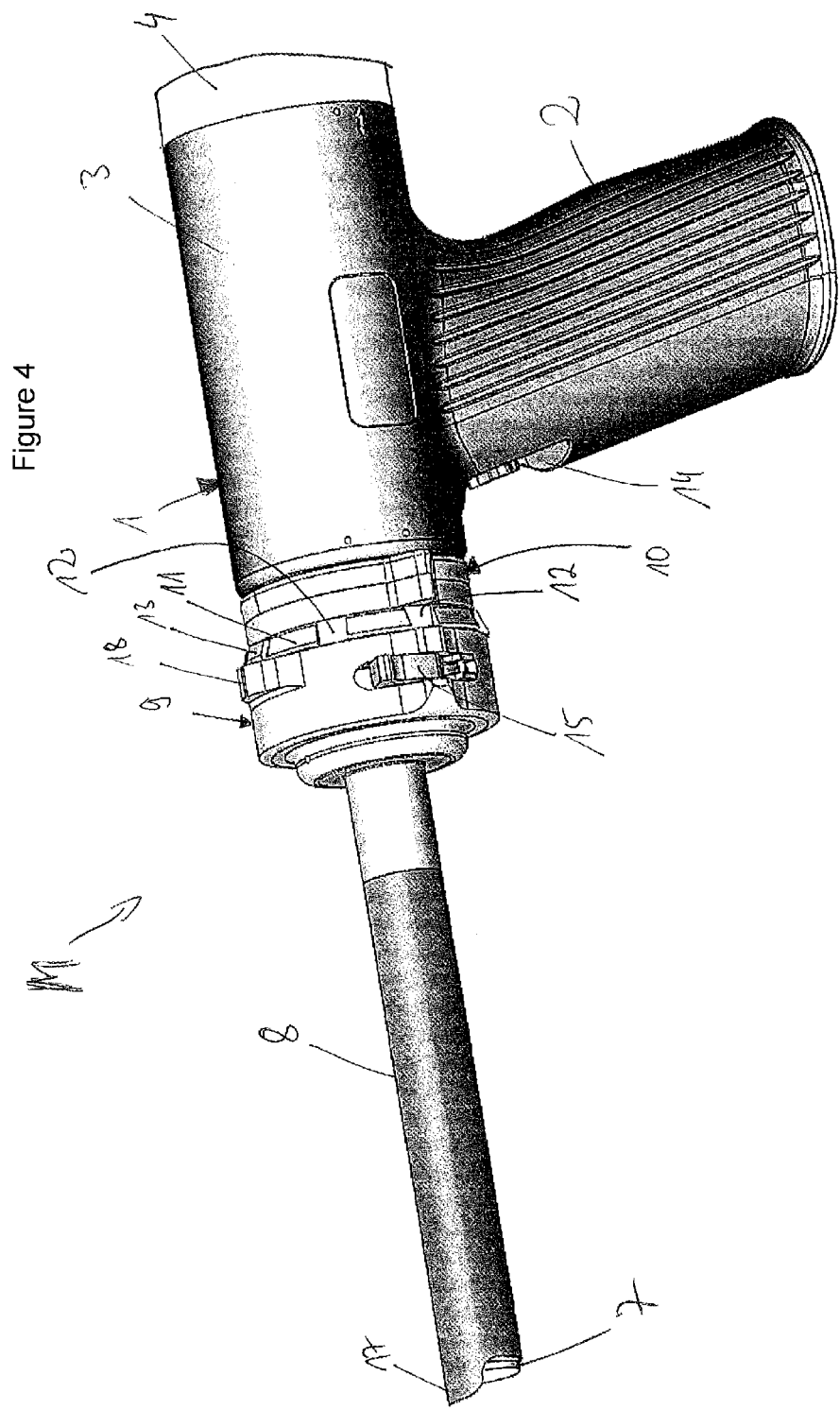
FIG. 4: shows an assembled morcellator.

Finally, it is shown in FIG. 4 how the connecting ring 9 has been connected to the connecting piece 10. The flange cam 13 now engages here in a predefined recess 12 of the connecting piece 10, wherein the bead 18 in this case always shows the precise position of the covering 17. In FIG. 4, the connecting piece 10 is not spaced apart from the hand module 1 by actuation of the actuating button 14, and therefore the cutting edge 7 partially protrudes at the distal end from the sleeve 8 to the extent that said cutting edge is not covered by the covering 17.

Figure 5:
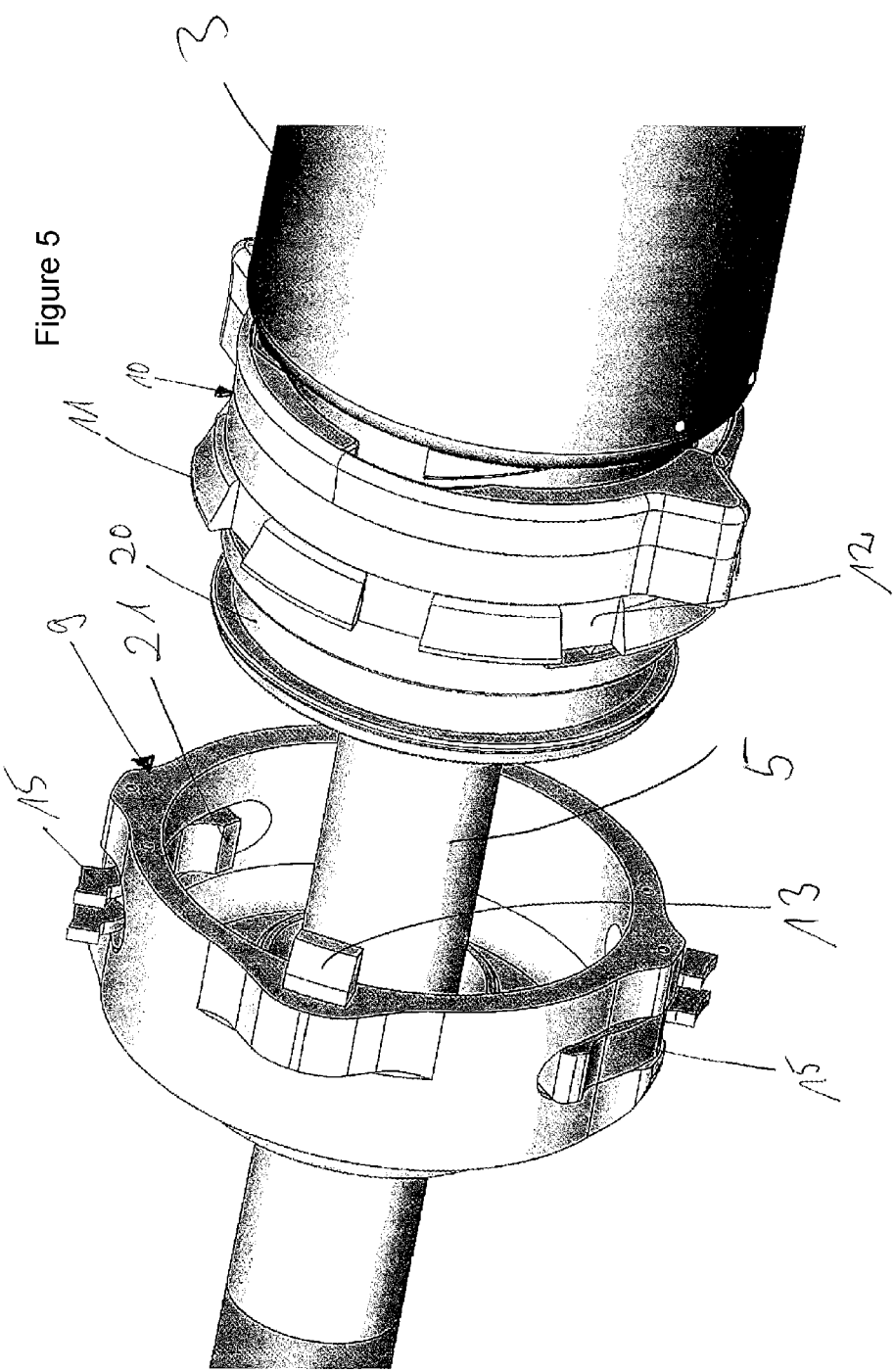
FIG. 5: shows another enlarged view of part of FIG. 3.

FIG. 5 once again shows an enlarged detailed view of FIG. 3 from a different perspective. For example, it can readily be seen there how the rocker latch 15 has a snap 21 which then engages in the groove 20 of the connecting piece 10.

In the use position, the valve module 4 is inserted into an open end of the guiding part 3 and the cutting tube 5 is inserted into the other open end, wherein the cutting tube has the cutting edge 7 at the other end of the driving connection 6. The drive is located in the handle part 2. Said drive interacts with a ring bevel gear which surrounds a receiving element in the guiding part of the hand module 1, wherein a latching cam of annular configuration engages in a corresponding ring groove in the receiving element. Said ring groove in turn forms an annular latching cam into the interior of the receiving element.

In the use position, the ring bevel gear engages by means of an internal toothed ring over an external toothed ring which is placed thereon as the cutting tube 5. By this means, a rotational movement of the bevel driving gear is transmitted via the ring bevel gear to the external toothed ring and the cutting tube 5 is rotated about the longitudinal axis thereof.

Furthermore, it can be seen that the cutting tube 5 is insertable releasably via a latching connection into the hand module 1 or the receiving element. For this purpose, a latching spring 16 protrude from the cutting tube 5 and, in the assembled position, engage behind the latching groove, which protrudes inward as the latching cam.

After the cutting tube 5 is inserted into, for example, a human body in order to remove tissue, for example through a trocar, the drive or the axis of rotation thereof is set into rotation via a pushbutton. At the same time, the bevel driving gear also rotates and, via the ring bevel gear, the internal toothed ring and the external toothed ring thereof, drives the cutting tube 5 or sets the latter into a rotational movement.

Should it be necessary, a further surgical instrument can be inserted through a corresponding valve in the valve module 4, said surgical instrument then also being able to be guided through the cutting tube 5 as far as the distal end thereof.

According to the invention, a cutting edge is located at the distal end of the cutting tube 5. Within the scope of the present invention, said cutting edge is formed from spring steel and rolled together to form a sleeve.

Reference is otherwise made with regard to the details to the disclosure of DE 10 2010 037 974 A1. A morcellator according to the invention is described there.

Figure 6:
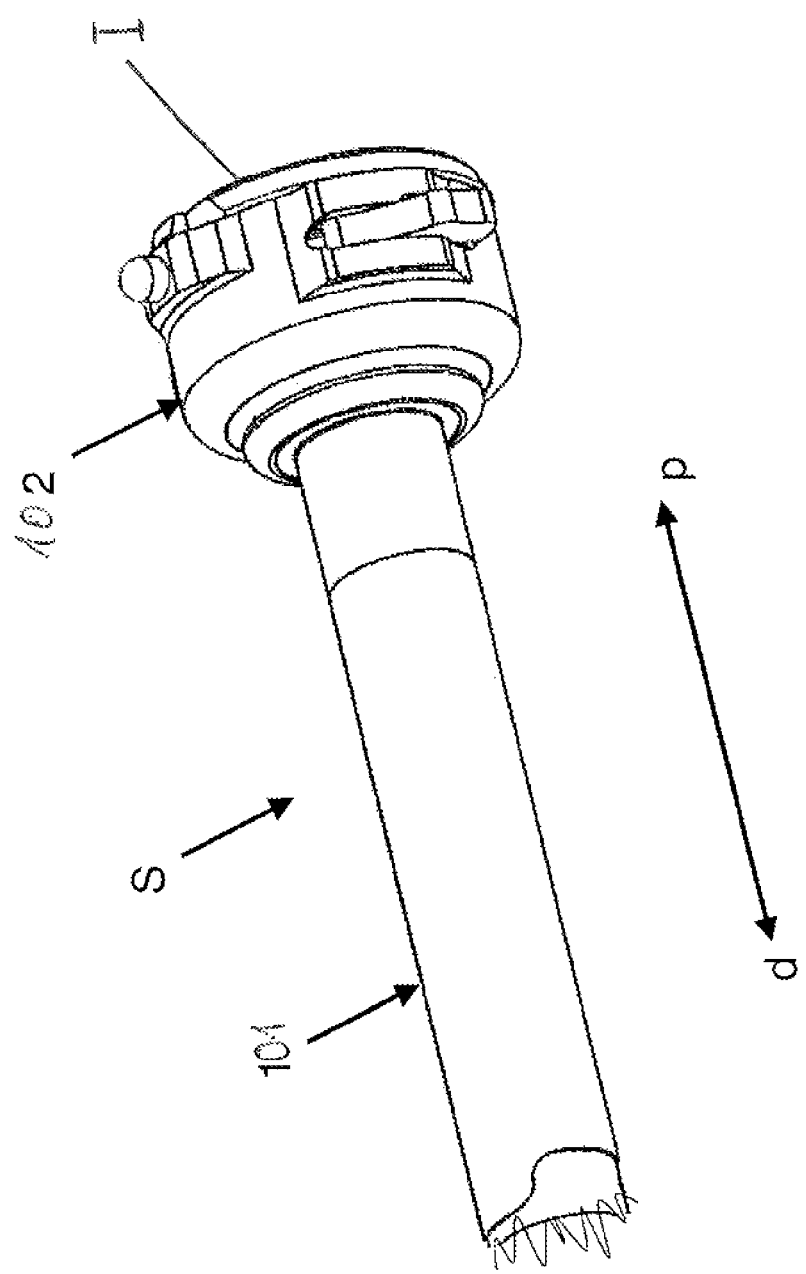
FIG. 6: shows a perspective view of a protective sleeve S with a medical instrument I located therein in the use position.

FIG. 6 illustrates a protective sleeve S with a medical instrument I located therein in the use position. The protective sleeve S comprises a tube 101 and a connecting device 102 at the proximal end.

Figure 7:
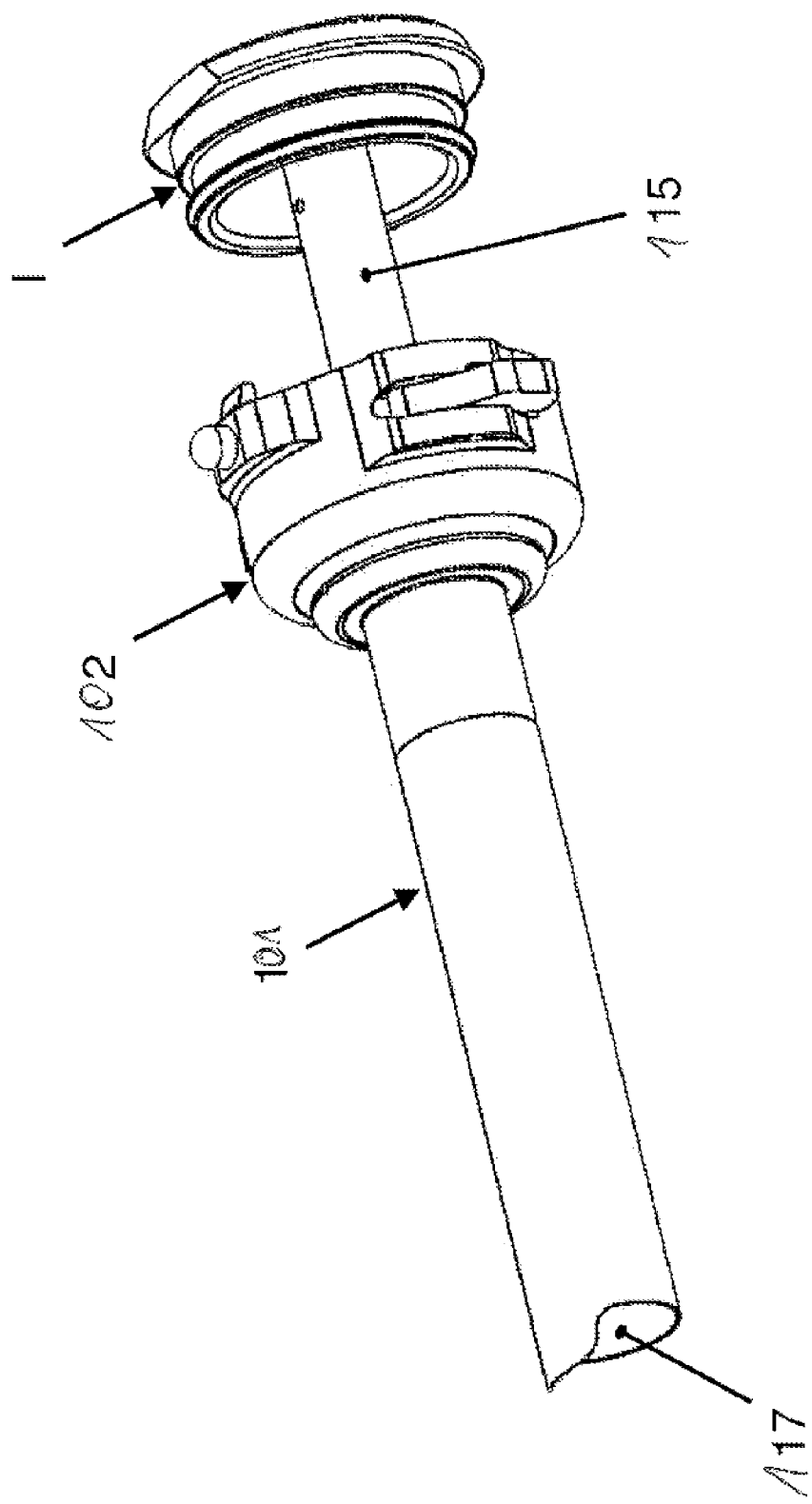
FIG. 7: shows a protective sleeve S and a medical instrument I with a shaft 15 according to FIG. 6 in the starting position.

FIG. 7 shows a protective sleeve S and a medical instrument I according to FIG. 6 in the starting position. Furthermore, a shaft 115 and a cavity 117 are shown in FIG. 7.

Figure 8:
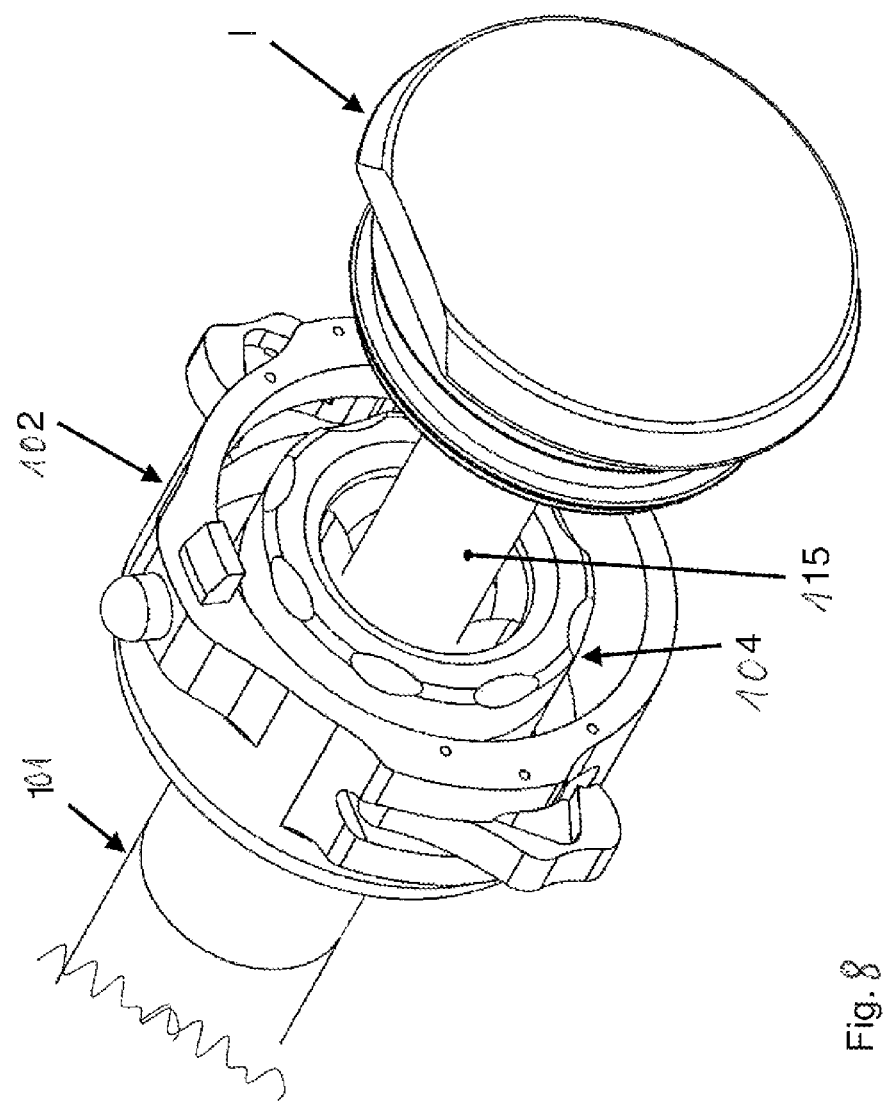
FIG. 8: shows a perspective partial view of the proximal end of the protective sleeve S according to FIG. 6, FIG. 9: shows a view according to FIG. 8 in the starting position without a medical instrument I.

FIG. 8 shows a perspective partial view of the proximal end of the protective sleeve S according to FIG. 6 in the starting position. The connecting device 102 and a valve 104 substantially surrounded by the latter can clearly be seen.

Figure 9:
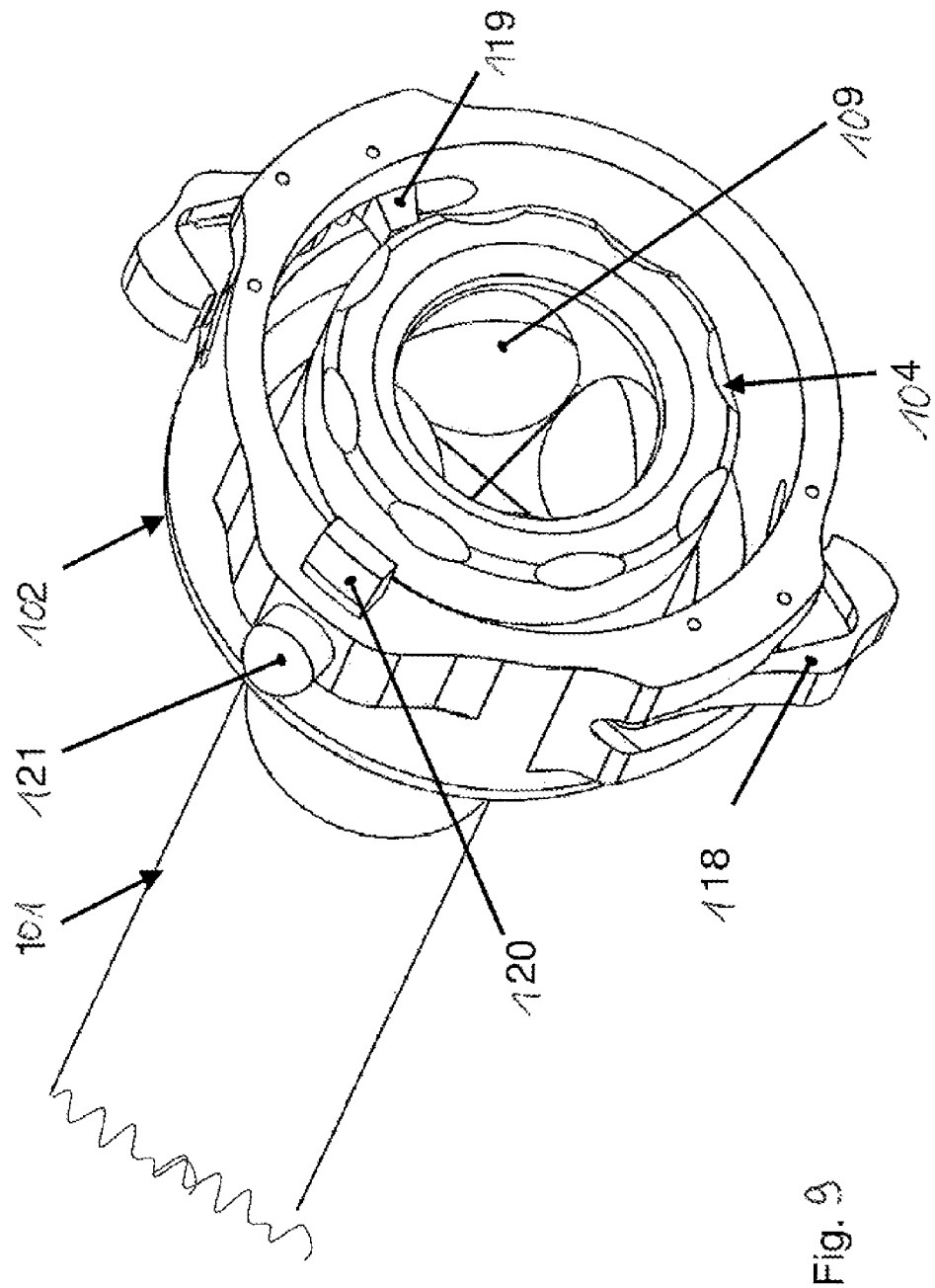

FIG. 9 illustrates a view according to FIG. 8 in the starting position without a medical instrument I. A sealing unit 109 of the valve 104 can be seen. A cam 120 is integrally formed on the connecting device 102. Furthermore, rocker latches 118 with snaps 119 are assigned to said connecting device.

Figure 10:
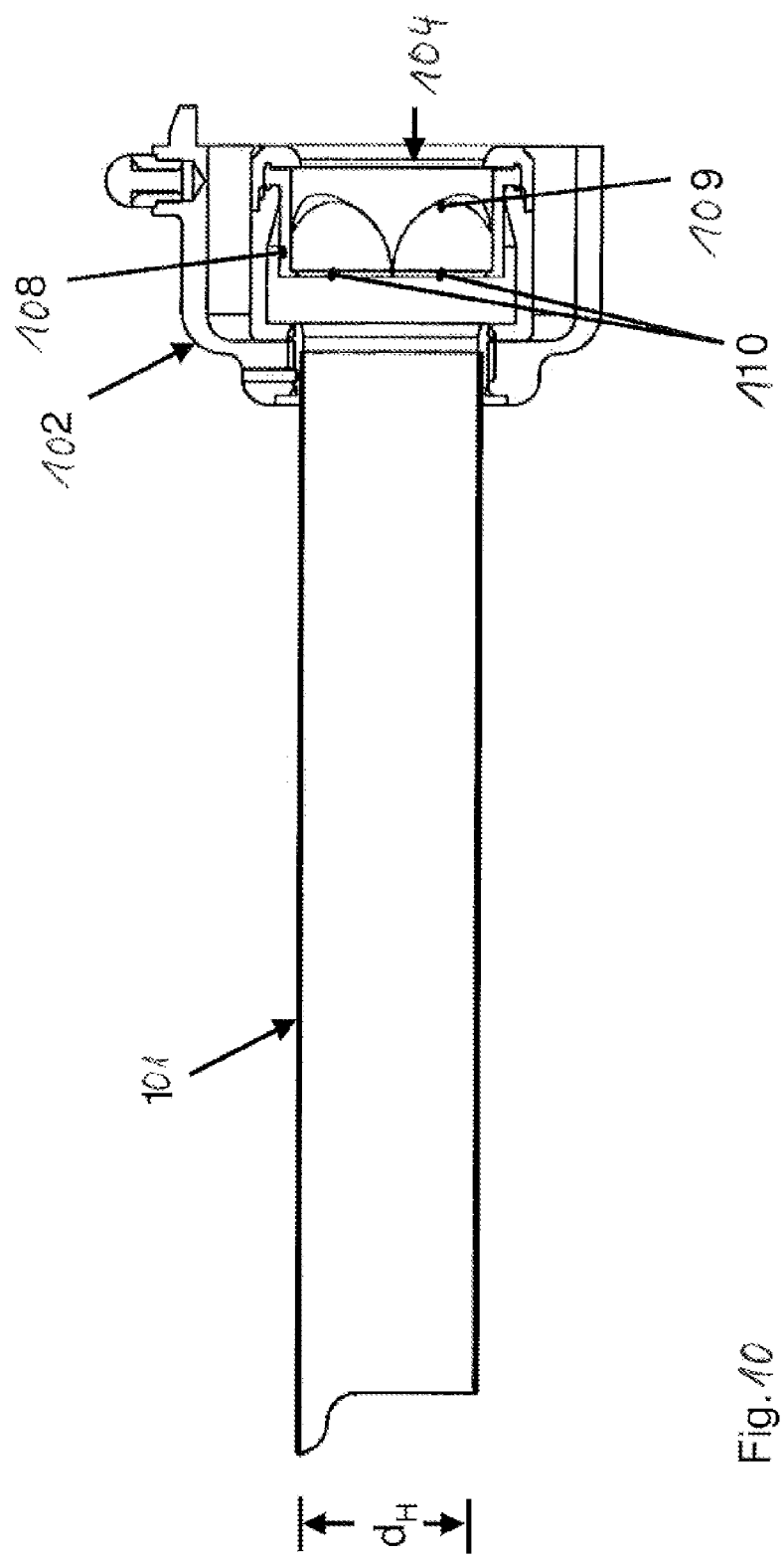
FIG. 10: shows a sectioned side view of a protective sleeve S in the starting position.

FIG. 10 shows a sectioned side view of a protective sleeve S in the starting position. The sealing unit 109 with the sealing lips 110 is located in the interior of a receptacle 108 of the valve 104. Furthermore, a diameter of the cavity dH is shown.

Figure 11:
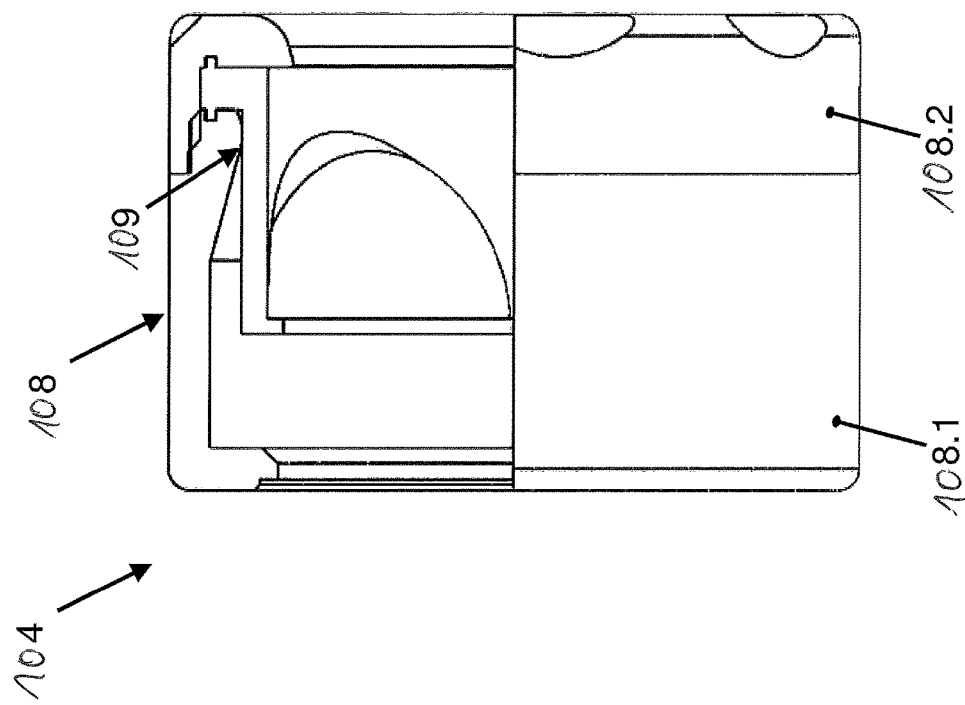
FIG. 11: shows a partially sectioned side view of a valve 4 in the starting position.

FIG. 11 shows a partially sectioned side view of a valve 104 in the starting position. An upper part 108.2 and a lower part 108.1 together form the receptacle 108. In addition, a sealing unit 109 is shown.

Figure 12:
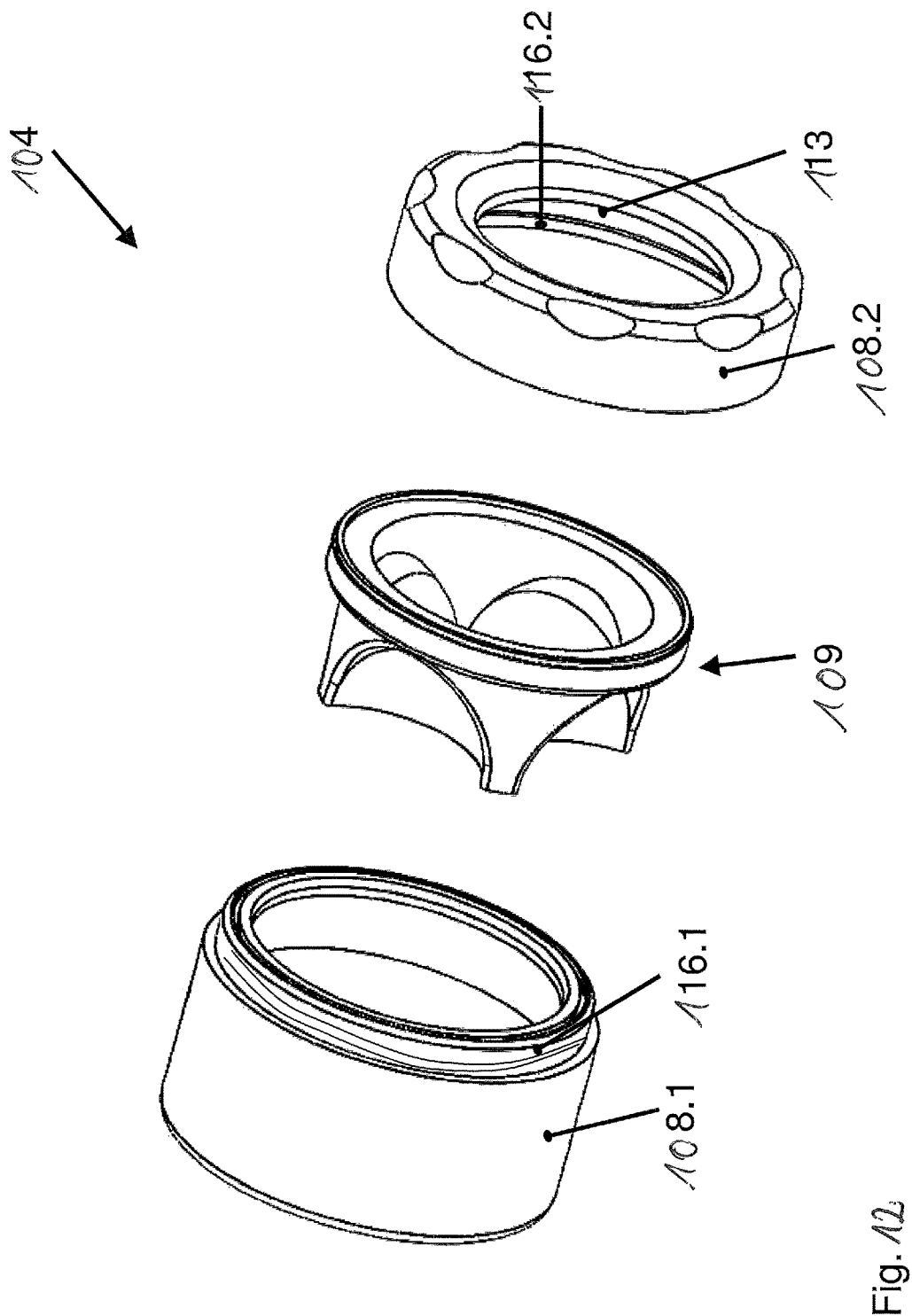
FIG. 12: shows a perspective view of a valve 4 in the disassembled state.

FIG. 12 illustrates a perspective view of a valve 104 in the disassembled state. An external thread 116.1 is integrally formed on the lower part 108.1. An internal thread 116.2 is integrally formed on the upper part 108.2 for its part. Also shown is the sealing unit 109 which is arranged between the lower part 108.1 and the upper part 108.2. When the lower part 108.1 and the upper part 108.2 are screwed to each other, the sealing unit 109 is secured between the lower part 108.1 and the upper part 108.2.

Figure 13:
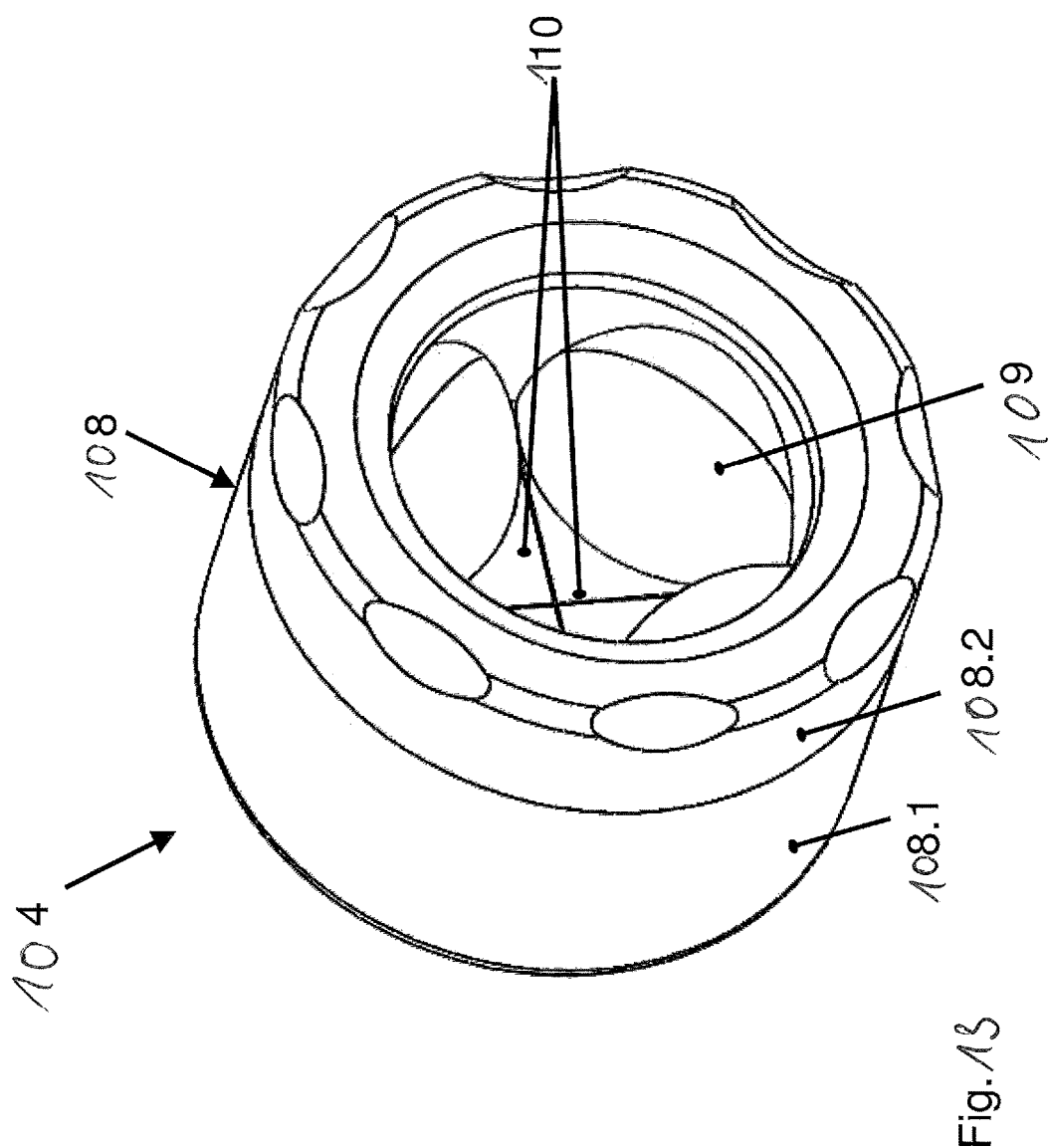
FIG. 13: shows a perspective view of a valve 4 in the assembled state.

FIG. 13 shows a perspective view of a valve 104 in the assembled state with touching sealing lips 110 when the lower part 108.1 and the upper part 108.2 are screwed to each other and secure the sealing unit 109 inbetween.

Figure 14:
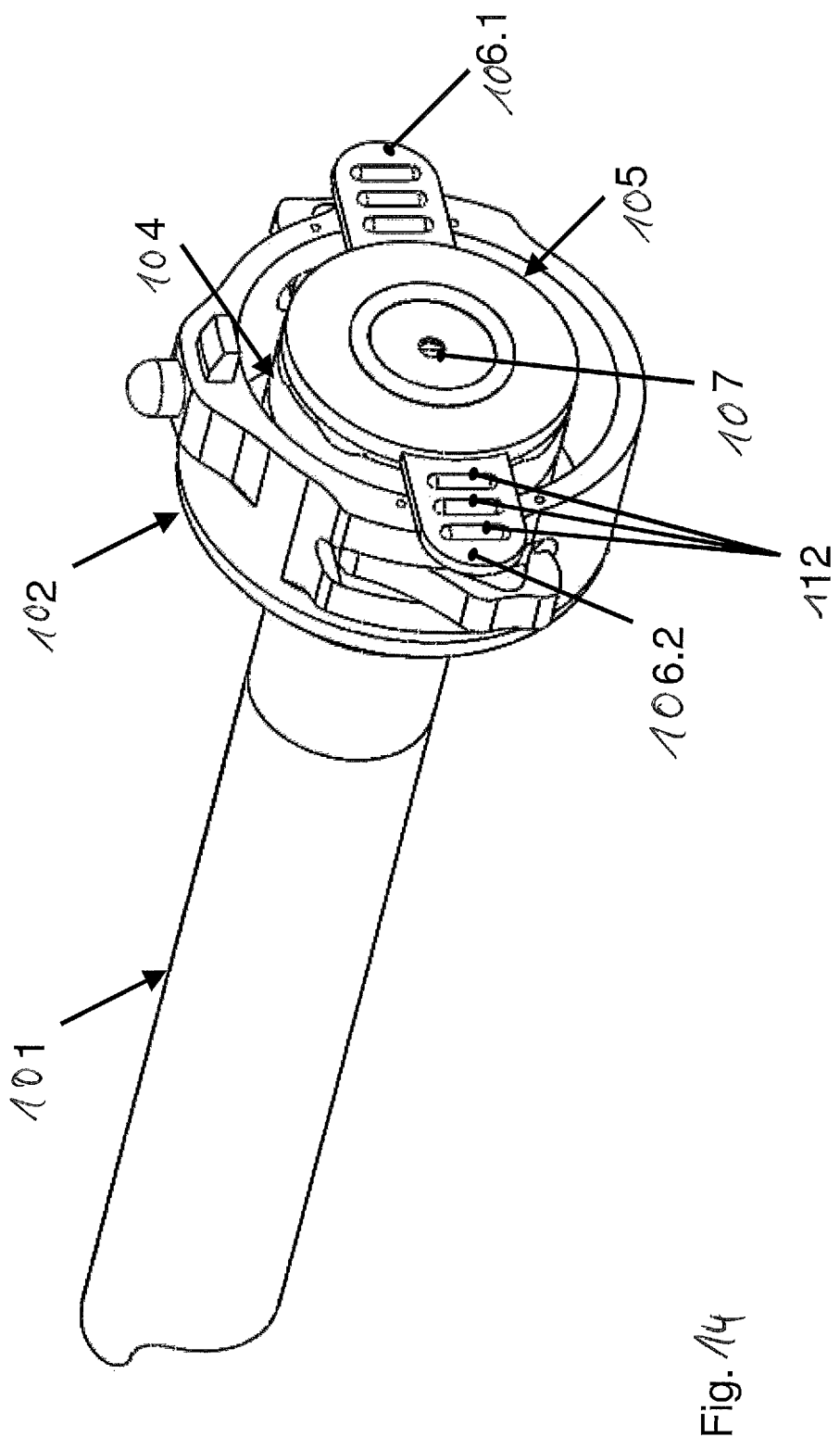
FIG. 14: shows a perspective view of a protective sleeve S with valve 4 and sealing element 5 in a first starting position.

FIG. 14 shows a perspective view of a protective sleeve S with valve 104 and sealing element 105 in a first starting position. The sealing element 105 is connected to the valve 104. Tabs 106.1, 106.2 which have elevations 112 are integrally formed laterally on the sealing element 105. The sealing element 105 has a recess 107 in the center.

Figure 15:
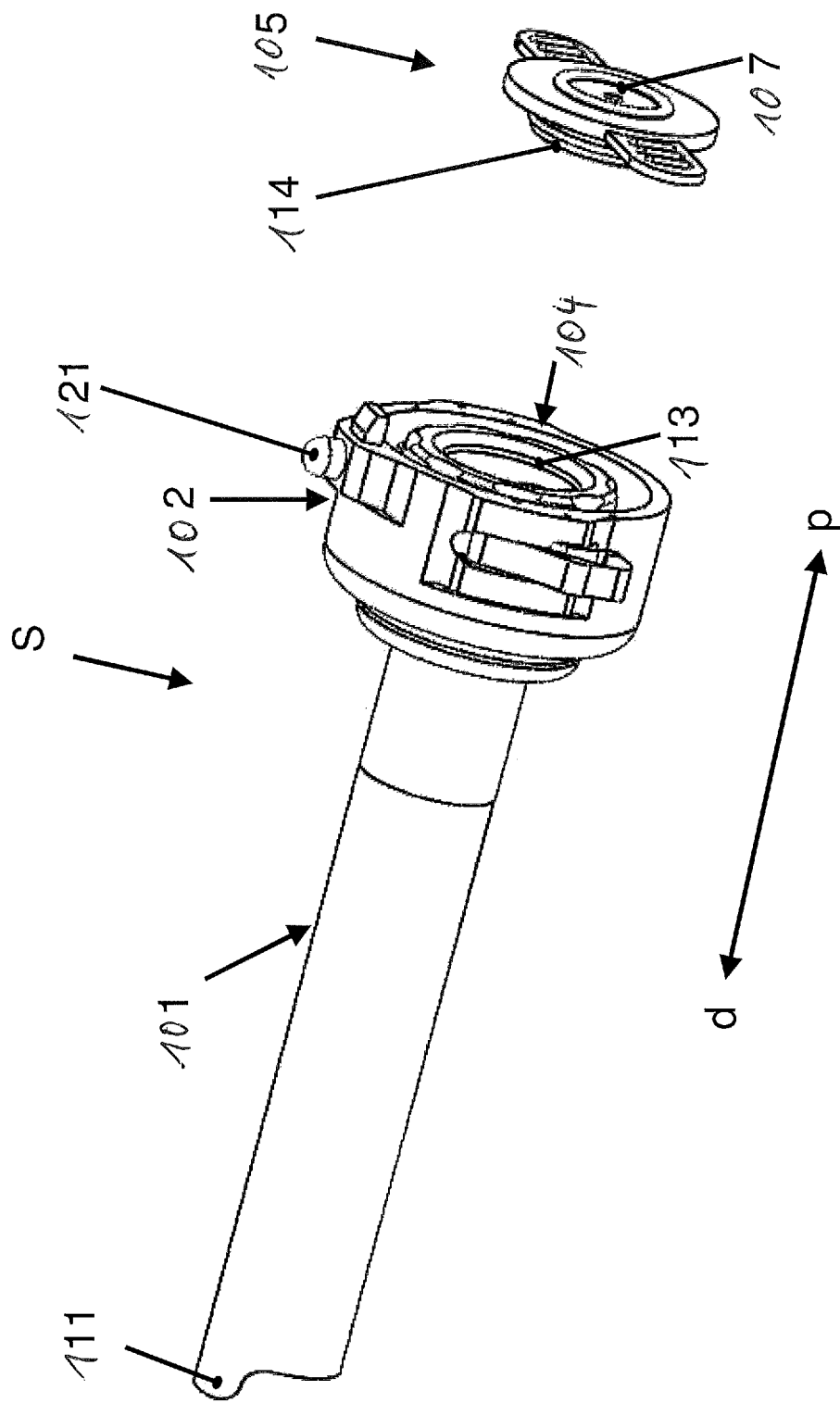
FIG. 15: shows a perspective view of a protective sleeve S with valve 4 and sealing element 5 in a second starting position.

FIG. 15 is a perspective view of a protective sleeve S with valve 104 and sealing element 105 in a second starting position. A groove 113 of the valve 104 and a bead 114 of the sealing element 105 can clearly be seen.

The manner of operation of the apparatus according to the invention is explained with respect to FIGS. 6-15 as follows:

The protective sleeve S serves for receiving a medical or surgical instrument I (not shown specifically). Within the scope of a minimally invasive operation, the tube 101 produces the connection between a location of the operation, at which, for example, tissue is removed, i.e., for example, a body cavity of a patient, and an operating theater or an environment around the patient. The tube 101 here surrounds a medical instrument I and at the same time shields intact tissue of the patient from the medical instrument I.

If, as can be seen in FIGS. 9 and 10, a medical instrument I is not introduced into the protective sleeve S, the sealing lips 110 of the sealing unit 109 close the valve 104. A gas located in the body cavity is therefore prevented from passing through from the distal to the proximal end of the protective sleeve S.

For the purpose of exchange or cleaning, the upper part 108.2 and lower part 108.1 of the valve 104, which parts are provided with corresponding threads 116.1, 116.2, can be separated. The sealing unit 109 can be cleaned or exchanged.

When the need arises, the sealing element 105 can be placed on the valve 104. A connection of the two parts is brought about by interaction of a bead 114 of the sealing element with a groove 113 of the valve 104. In order to connect sealing element 105 and valve 104, the sealing element 105, which is composed of flexible material, is introduced in the distal direction into a proximal end of the valve 104. The recess 107 of the sealing element 105 permits a medical or, for example, optical instrument with a cross section which is very small compared to the cross section of the cavity 117 of the tube 101 to be guided. An instrument is therefore guided substantially coaxially with an imaginary longitudinal axis of the tube 101. Furthermore, the sealing element 105 permits additional sealing of two spaces located on the other side of distal and proximal end of the protective sleeve S, for example operating theater and body cavity, by a shaft diameter of the instrument and a diameter of the recess 107 of the sealing element 105 being selected in such a manner that an instrument introduced into the recess 107 can prevent gas from passing through the recess 107.

A surgeon can easily release the positive connection between sealing element 105 and valve 104 again, even during an operation, by means of the tabs 106.1, 106.2. The elevations 112 on the tabs 106.1, 106.2 are helpful here since they prevent the surgeon's fingers from slipping off or provide a secure grip.

In order to connect the protective sleeve S to a handpiece (not illustrated), the cam 120 can be introduced into a recess (not illustrated) of the handpiece. This prevents an undesirable rotation of the protective sleeve S in relation to the handpiece during an operation. The connection between handpiece and protective sleeve S is provided by rocker latches 118, at one end of which snaps 119 are integrally formed. The snaps 109 can engage in a groove (not shown) of the handpiece and can connect the protective sleeve S to the handpiece. A position indicator 121 is expedient if, for example, a covering 111 is present. If position indicator 121 and covering 111 are located in one plane in an imaginary longitudinal section through the protective sleeve S, the surgeon can then always see, by means of the position indicator 121 located outside the body cavity during an operation, where the covering 111 is located.

The invention claimed is:

1. A connecting element for a morcellator, wherein the morcellator has a hand module, a cutting tube and a sleeve, the connecting element comprising a connecting piece configured to be attached to the hand module and a connecting ring configured to be connected to the sleeve, wherein the connecting ring is adapted to be clipped onto the connecting piece, wherein the connecting ring defines a central axis and has a rocker latch which serves for securing the connecting ring on the connecting piece, wherein the rocker latch is adapted to engage a groove of the connecting piece, and wherein the rocker latch is pivotable around an axis which is parallel to the central axis between a position engaged in the groove and a position removed from the groove.

2. The connecting element as claimed in claim 1, wherein the connecting piece has a flange-mounted ring having a recess, wherein a flange cam of the connecting ring can be brought into engagement non-rotatably in the recess by clipping the connecting ring onto the connecting piece.

3. The connecting element as claimed in claim 2, wherein the flange cam has a covering configured to be in an extension of a circumference of the sleeve, wherein the flange cam and the covering substantially form a line.

4. The connecting element as claimed in claim 3, wherein the covering is configured to have at a distal end a partial extension of the sleeve over part of the circumference of the sleeve.

5. The connecting element as claimed in claim 3, wherein the flange cam has a position indicator in the form of a bead, the bead indicates the position of the flange cam and of the covering.

6. The connecting element as claimed in claim 1, wherein the cutting tube is adapted to be clipped to the hand module via a latching cam.

7. The connecting element as claimed in claim 1, wherein the connecting piece is movable toward and away from the hand module by an actuating button.

8. The connecting element as claimed in claim 7, wherein the actuating button is configured to bring about a screwing movement of the connecting piece on the hand module and therefore achieves a spacing.

9. The connecting element as claimed in claim 7, wherein the actuating button, by moving the connecting piece away from the hand module, also moves the connecting ring away from the hand module, wherein the sleeve can be pushed over a cutting edge of the cutting tube.

10. The connecting element as claimed in claim 7, wherein the actuating button, by moving the connecting piece toward the hand module, also moves the connecting ring toward the hand module, wherein the sleeve releases a cutting edge of the cutting tube.

\* \* \* \* \*